US009233084B2

(12) United States Patent
Rana et al.

(10) Patent No.: US 9,233,084 B2
(45) Date of Patent: Jan. 12, 2016

(54) CALCIUM CARBONATE MICROSTRUCTURES USEFUL IN ENCAPSULATION APPLICATIONS AND A PROCESS FOR THE PREPARATION THEREOF

(75) Inventors: Rohit Kumar Rana, Hyderabad (IN); Gousia Begum, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 244 days.

(21) Appl. No.: 13/045,757

(22) Filed: Mar. 11, 2011

(65) Prior Publication Data
US 2011/0223111 A1    Sep. 15, 2011

(30) Foreign Application Priority Data
Mar. 12, 2010 (IN) .............................. 572/DEL/2010

(51) Int. Cl.
*A61K 31/155* (2006.01)
*A61K 31/65* (2006.01)
*A61K 31/704* (2006.01)
*A61K 49/00* (2006.01)

(52) U.S. Cl.
CPC ............... *A61K 31/155* (2013.01); *A61K 31/65* (2013.01); *A61K 31/704* (2013.01); *A61K 49/0043* (2013.01); *A61K 49/0054* (2013.01); *A61K 49/0091* (2013.01)

(58) Field of Classification Search
CPC combination set(s) only.
See application file for complete search history.

(56) References Cited

U.S. PATENT DOCUMENTS 7,090,868 B2 *   8/2006   Gower et al. .................. 424/489

OTHER PUBLICATIONS

Loges et al., Langmuir 2006, 22, 3073-3080.*
Sugihara et al., J. Ceramic Soc. Of Japan, 105 [10], 886-890 (1997).*
Sukhorukov et al., J. Mater. Chem., 2004 14, 2073-2081.*
Mrinmoy DE, et al; "Applications of Nanoparticles in Biology", Advanced Materials vol. 20, Issue 22, pp. 4225-4241; first published online Aug. 27, 2008.
Thomas E. Rams, et al; "Local delivery of antimicrobial agents in the periodontal pocket", Periodontology 2000 vol. 10, pp. 139-159, Feb. 1996.
T.C. Yih, et al; "Engineered Nanoparticles as Precise Drug Delivery Systems", Journal of Cellular Biochemistry, vol. 97, Issue 6, pp. 1184-1190; Article first published online: Jan. 26, 2006.
Jayanth Panyam, et al; "Biodegradable nanoparticles for drug and gene delivery to cells and tissue", Advanced Drug Delivery Reviews, vol. 55, pp. 329-347, Feb. 24, 2003

H.T. Schmidt, et al; "Antibody-conjugated soybean oil-filled calcium phosphate nanoshells for targetted delivery of hydrophobic molecules", Journal of Microencapsulation, vol. 23, Issue 7, Nov. 2006, pp. 769-781.
Yoon Jeong Park et al; "Enhanced guided bone regeneration by controlled tetracycline release from poly(L-lactide) barrier membranes", J. Biomed Mater Res. Sep. 5, 2000; vol. 51, Issue 3, pp. 391-397.
Wendy L. Webber, et al; "Characterization of soluble, salt-loaded, degradable PLGA films and their release of tetracycline", J. Biomed Mater Res. Jul. 1998, vol. 41, Issue 1; pp. 18-29.
B. Bittner, et al; "Tetracycline-HCl-loaded poly(DL-lactide-co-glycolide) microspheres prepared by a spray drying technique: influence of γ-irradiation on radical formation and polymer degradation", Journal of Controlled Release, volume 59, Issue 1; May 1, 1999; pp. 23-32.
Kyriaki Kanellakopoulou, et al; "Carrier Systems for the Local Delivery of Antibiotics in Bone Infections" Drugs, Jun. 2000, vol. 59, Issue 6, pp. 1223-1232.
Benjamin Tycko, et al; "Rapid Acidification of Endocytic Vesicles Containing $\alpha_2$-Macroglobulin", Cell, vol. 28, Mar. 1982, pp. 643-651.
B. Kriwet, et al; "Interactions between bioadhesive poly(acrylic acid) and calcium ions", International Journal of Pharmaceutics vol. 127, Issue 2, Feb. 17, 1996, pp. 135-145.
Marion Stubbs, et al; "Causes and consequences of tumour acidity and implications for treatment", Molecular Medicine Today, Jan. 2000, vol. 6, pp. 15-19.
Larken E. Euliss, et al; "Control of calcium carbonate crystallization utilizing amphiphilic block copolypeptides", Journal of Crystal Growth, vol. 286, pp. 424-430, Available online Dec. 2, 2005.
Lars Sonnenberg, et al; "Quantitative Single Molecule Measurements on the Interaction Forces of Poly(L-glutamic acid) with Calcite Crystals", Journal American Chemical Society, vol. 129, pp. 15364-15371; Published on Web Nov. 16, 2007.
Brandon J. McKenna, et al; "Micrometer-Sized Spherical Assemblies of Polypeptides and Small Molecules by Acid-Base Chemistry", Angew Chem Int Ed Engl. Oct. 25, 2004, vol. 43, Issue 42; pp. 5652-5655.
Lia Addadi, et al; "Taking Advantage of Disorder: Amorphous Calcium Carbonate and Its Roles in Biomineralization", Advanced Materials, Jun. 17, 2003, vol. 15, No. 12, pp. 959-970.

(Continued)

*Primary Examiner* — Michael G Hartley
*Assistant Examiner* — Robert Cabral
(74) *Attorney, Agent, or Firm* — Ladas & Parry LLP (57) ABSTRACT

A facile method to synthesize stable calcium carbonate microstructures is demonstrated which allows in situ encapsulation of sensitive molecules like drugs. The methodology involves a macromolecular assembly of anionic polypeptide with cationic peptide oligomer to concurrently template and hold to stabilize the mineralized structure. The heterogeneously distributed mixture of anionic and cationic residues in the macromolecular assembly, similar to that is found in natural systems assists in recognizing and coassembling $Ca^{2+}$ and $CO_3^{2-}$ ionic clusters, especially for formation of a disordered precursor phase such as amorphous calcium carbonate (ACC) and further crystallization to form a metastable vaterite phase. The assembly also facilitates encapsulation of a guest molecule such as tetracycline at ambient conditions without affecting the mineralization process. The tetracycline-loaded microstructures show excellent antibacterial activities against many Gram-positive and Gram-negative bacterial strains and hence together with the fluorescence property of tetracycline and appropriate drug release profile, they can be used as multifunctional materials for therapeutic and imaging applications.

7 Claims, 6 Drawing Sheets

(56) References Cited

OTHER PUBLICATIONS

Shu-Chen Huang, et al; "A Carbonate Controlled-Addition Method for Amorphous Calcium Carbonate Spheres Stabilized by Poly(acrylic acid)s", Langmuir, vol. 23, pp. 12086-12095, Published on Web Oct. 27, 2007.

Giuseppe Falini, et al; "Control of Aragonite or Calcite Polymorphism by Mollusk Shell Macromolecules", Science, vol. 271, Jan. 5, 1996, pp. 67-69.

A.M. Belcher, et al; "Control of crystal phase switching and orientation by soluble mollusk-shell proteins", Nature, vol. 381, May 2, 1996, pp. 56-58.

C.A. Orme, et al; "Formation of chiral morphologies through selective binding of amino acids to calcite surface steps", Nature, vol. 411, Jun. 14, 2001, pp. 775-779.

Nicole Gehrke, et al; "Retrosynthesis of Nacre via Amorphous Precursor Particles", Chem. Mater, vol. 17, pp. 6514-6516, Published on Web Dec. 3, 2005.

Lijun Dai, et al; "Transition Bars during Transformation of an Amorphous Calcium Carbonate Precursor", Chem. Mater. vol. 20, pp. 6917-6928, Published on Web Oct. 29, 2008.

M.E. Linday, "Practical Introduction to Microbiology", London: E & F.N Spon Ltd; p. 177, Dec. 1962.

Matthew A Wikler, et al; "Methods for Dilution Antimicrobial Susceptibility Tests for Bacterial that Grow Aerobically; Approved Standard-Eighth Edition", vol. 29, No. 2, NCCLS, Villanova, PA., 2009, Approved Standard M07-A8, 10 pages.

Zhongping Zhang, et al; "Biomimetic Assembly of Polypeptide-Stabilized $CaCO_3$ Nanoparticles", J. Phys. Chem. B, vol. 110, pp. 8613-8618, Published on Web Apr. 7, 2006.

* cited by examiner

CALCIUM CARBONATE MICROSTRUCTURES USEFUL IN ENCAPSULATION APPLICATIONS AND A PROCESS FOR THE PREPARATION THEREOF

FIELD OF THE INVENTION

The present invention provides calcium carbonate microstructures useful in encapsulation applications and a process for the preparation thereof. More particularly, the present invention relates to a preparation of calcium carbonate microstructure, which is easily adaptable for encapsulation of guest molecules during the synthesis.

BACKGROUND OF THE INVENTION

Substantial use of drugs such as antibiotics can cause several side effects after their absorption into the blood stream; one of them is bacterial resistance. So, it is highly desirable to develop methods of local administration of antibiotics. Such administration makes it possible to apply higher concentration of drug in the target tissue and the influence of systematic administration significantly decreases. The field of nanotechnology in this respect offers a promising approach to develop nanostructured materials for biomedical applications [De, M.; Ghosh, P. S.; Rotello, V. M. Adv. Mater. 2008, 20, 1-17]. These systems present advantages over systemic administration, such as a considerably increased and sustained drug concentration in the crevicular fluid, as well as a reduction of other undesirable side effects associated with systemic drug delivery devices [Rams, T. E.; Slots, J. Periodontology 2000, 1996, 10, 139-159]. Also, the major drawback associated with many of therapeutics is their poor bioavailability and toxicity [(a) Yih, T. C.; Al-Fandi, M.; J. Cell. Biochem. 2006, 97, 1184; (b) Panyam, J.; Labhasetwar, V. Adv. Drug Delivery Rev. 2003, 55, 329]. Therefore, encapsulation of such therapeutics in a pH tunable soluble capsules can provide a novel means of transportation to specific cells or tissues [Schmidt, H. T.; Kroczynski, M.; Maddox, J.; Chen, Y.; Josephs, R.; Ostafin, A. E. J. Microencapsulation 2006, 23, 769].

Tetracycline is one of the most potent broad spectrum therapeutic molecules, which is used extensively to treat bacterial infections associated with bone diseases. It is effective against both gram-positive and gram-negative microorganisms. Local administration of tetracycline is recognized to increase bone regeneration in periodontal defects due to its anti-collagenolytic effect. It also promotes the growth of alveolar bone in periodontal therapy [Park. Y. J.; Lee, Y. M.; Park, S. N.; Lee, J. Y.; Ku, Y.; Chung, C. P.; Lee, S. J. J Biomed Mater Res, 2000, 51, 391]. Therefore controlled delivery of tetracycline may be highly beneficial for the treatment of infectious bone diseases. Various matrices for encapsulation and controlled release of tetracycline includes poly(L-lactide) fibers, PLGA films [Webber, W. L.; Lago, F.; Thanos, c.; Mathiowitz, E. J. Biomed. Mater. Res. 1998, 41, 18] and chitosan microspheres [Bittner, B.; Mäder, K.; Kroll, C.; Borchert, H.-H.; Kissel, T. J. Controlled Release 1999, 59, 23]. Although poly(methyl methacrylate) beads are widely used for treatments, its removal after exhaustion of the antibiotic activity has been a major drawback [Kanellakopoulou, K.; Giamarellos-Bourboulis, E. J. Drugs 2000, 59, 1223].

The drawbacks of the processes are that the methodology is generally tedious sometimes requiring harsh reaction conditions such as extreme pH and higher temperature, organic solvents, emulsion methods, and post-treatments to encapsulate the drug, which may affect the drug stability and efficacy.

$CaCO_3$ when compared to other inorganic materials is ideal as drug delivery system for much therapeutics because of its pH tunable solubility, biocompatibility and biodegradability. As a biomineral $CaCO_3$ is bioresorbable and insoluble at physiological pH but soluble under acidic conditions. The pH around many of the tumors and endolysosomes is acidic [(a) Tycko, B.; Maxfield, F. R. Cell 1982, 28, 643-651; (b) Stubbs, M.; McSheehy, P. M.; Griffiths, J. R.; Bashford, C. L. Mol. Med. Today 2000, 6, 15-19]. Therefore, $CaCO_3$ can be used as a pH-dependent vehicle to deliver the therapeutics through the blood stream to target tissue.

Ideally, the methodology to prepare the host matrix $CaCO_3$ should allow the drug encapsulation during the synthesis of the inorganic host thereby avoiding the post-treatments generally required for inserting the drugs into various matrices. Herein we demonstrate such a facile one-pot synthesis of $CaCO_3$ microstructures under very mild conditions of ambient temperature and pressure, aqueous medium and near neutral pH. The methodology utilizes the self assembly property of polyanions in presence of suitable counter ions to mineralize $CaCO_3$ structures while simultaneously facilitating the entrapment of tetracycline in situ.

It is known that carboxyl groups of biomicromolecules play a crucial role in polymorph stabilization of $CaCO_3$. The carboxylate groups of anionic residues interact with $Ca^{2+}$ due to charge matching and induce nucleation [(a) Kriwet, B.; Kissel, T. Int. J. Pharm. 1996, 127, 135-145; (b) Euliss, L. E.; Bartl, M. H.; Stucky, G. D. J. Cryst. Growth, 2006, 286, 424; (c) Sonnenberg, L.; Luo, Y.; Schlaad, H.; Seitz, M.; Cö lfen, H.; Gaub, H. E. J. Am. Chem. Soc. 2007, 129, 15364].

Here in present application, the approach is to use anionic polypeptides to interact ionically with cationic peptide oligomers to form assembled structures, which effectively can act as a mold and thereby, dictate the morphology of the mineralized $CaCO_3$. Such phenomena of macromolecular assemblies have been known in the literature [McKenna, B. J.; Birkedal, H.; Bartl, M. H.; Deming, T. J.; Stucky, G. D. Angew. Chem. Int. Ed., 2004, 43, 5652-5655]. However utilization of these assembled structures to mineralize $CaCO_3$ microstructures is the new and nonobvious invention of this patent work. It is shown here that these mineralizing agents aid in controlled crystallization of $CaCO_3$ and can stabilize amorphous and vaterite phases, the thermodynamically less stable polymorphs of $CaCO_3$. More importantly, the methodology allows guest molecules like drugs to be loaded into these microstructures during the preparation.

OBJECTIVES OF THE INVENTION

The main object of the present invention is to provide calcium carbonate microstructures useful in encapsulation applications and a process for the preparation thereof which obviates the drawbacks of the hitherto known prior art as detailed above.

Another object of the present invention is to provide a methodology to synthesize calcium carbonate microstructures under mild conditions such as room temperature and atmospheric pressure, aqueous medium, near neutral pH suitable for in-situ encapsulation of guest molecules.

Still another object of the present invention is to provide the methodology in which the mineralizing agents are entrapped in the structure to provide structural stability while they mineralize the formation of the calcium carbonate microstructures.

Yet another object of the present invention is to provide the methodology that allows for encapsulation of a guest molecule such as drug during the preparation of calcium carbonate microstructures Yet another object of the present invention is to provide calcium carbonate microstructures with activity such as therapeutic and imaging required in biomedical applications.

Yet another object of the present invention is to provide sustained and controlled release of the encapsulated guest molecule such as a drug from the calcium carbonate microstructures.

Yet another object of the present invention is to demonstrate the activity of the encapsulated guest molecule such as antibacterial activity of tetracycline loaded in calcium carbonate microstructures.

SUMMARY OF THE INVENTION

Accordingly, the present invention provides calcium carbonate microstructures useful in encapsulation applications and a process for the preparation thereof. The present invention provides comprises a facile methodology to synthesize calcium carbonate microstructures under mild reaction conditions such as 25-35° C., atmospheric pressure, aqueous medium and pH 6-8, in which a macromolecular assembly of anionic polymer such as polyanions, polypeptides etc. with multivalent cationic species such as cationic peptide oligomers, polyamines etc. mineralizes and templates the formation of calcium carbonate microstructures in an aqueous solution containing salts of $Ca^{2+}$ and salts of $CO_3^{2-}$, to encapsulate guest molecules, the guest molecules are added before addition of the salts of $Ca^{2+}$ and $CO_3^{2-}$ to form guest molecule loaded calcium carbonate microstructures which may display fluorescence either because of the entrapped dye conjugated polymer or dye conjugated multivalent cationic oligomer or the encapsulated guest molecule such as tetracycline as required for imaging applications, and the release profile shows a controlled and sustained drug release depending upon the salts present in the buffer used for the study or the pH of the medium and demonstrate antibacterial activity against various Gram-positive and Gram-negative bacterial strains.

The synthesized calcium carbonate microstructures is a stable, controlled release microstructure, having core-shell structure The calcium carbonate microstructures have morphology comprised of but not limited to a spherical morphology with a core-shell structure where in the core is comprised of the anionic polymer and multivalent cationic oligomer, and the shell is comprised of the anionic polymer, multivalent cationic oligomer and $CaCO_3$.

In an embodiment of the present invention, calcium carbonate microstructure comprises of an anionic polymer in the range of 9-12%, multivalent cationic oligomer in the range of 5-7% and $CaCO_3$ in the range of 76-81% by weight.

In an embodiment of the present invention, the anionic polymer is selected from the group consisting of poly(aspartate) and Fluorescein isothiocyanate (FITC)-tagged poly(aspartate) with a molecular weight of 5-50 kD, having concentration range of 1-5 mg/ml.

In an embodiment of the present invention, the multivalent cationic oligomer is selected from the group consisting of tetraethylenepentamine, penta(L-lysine) and Fluorescein isothiocyanate (FITC)-tagged penta(L-lysine), having concentration range of 1-5 mg/ml.

In another embodiment of the present invention, morphology of the calcium carbonate microstructure is spherical or doughnut.

In another embodiment of the present invention, the calcium carbonate spheres diameter ranges between 0.5-4.0 micrometers.

In another embodiment of the present invention, the calcium carbonate microstructures are mechanically stable under ultrasonication as compared to the structures obtained in absence of the cationic oligomer.

Another aspect of the present invention is a process for the preparation of calcium carbonate microstructures useful in encapsulation applications, wherein said process comprises the steps of:

a. mixing anionic polymer and multivalent cationic oligomer followed by aging for a period ranging between 0-30 minutes at temperature ranging between 25-35° C.;

b. adding aqueous solution of calcium salt with a concentration ranging between 0.01-0.1M and subsequently adding salt of carbonate with a concentration ranging between 0.01-0.1M;

c. aging the mixture as obtained in step (b) for a period ranging between 30 minutes-15 hours at room temperature ranging between 25-35° C. to get precipitate of calcium carbonate; separating calcium carbonate as obtained in step (c) by centrifugation at speed ranging between 8000-10000 rpm and washing with water followed by drying at room temperature ranging between 25-35° C. to obtain calcium carbonate microstructure.

In another embodiment of the present invention, the salts of $Ca^{2+}$ in step (b) are selected from the group consisting of chloride, sulfate and nitrate.

In another embodiment of the present invention, the salts of $CO_3^{2-}$ in step (b) are selected from the group consisting of ammonium, sodium and potassium.

In another embodiment of the present invention, wherein the anionic polymer used in step (a) is selected from the group of poly(aspartate) and Fluorescein isothiocyanate (FITC)-tagged poly(aspartate) with a molecular weight of 5-50 kD, having concentration range of 1-5 mg/ml.

In another embodiment of the present invention, wherein the multivalent cationic oligomer used in step (a) is selected from the group consisting of tetraethylenepentamine, penta (L-lysine) and Fluorescein isothiocyanate (FITC)-tagged penta(L-lysine) having concentration range of 1-5 mg/ml.

In another embodiment of the present invention, molar ratio of $Ca^{2+}:CO_3^{2-}$:poly(aspartate):penta(L-lysine) ranges between 1.0:1.0:0.04:0.02 to 1.0:1.0:0.7:0.96.

In yet another embodiment of the present invention, guest encapsulated calcium carbonate microstructure is prepared by addition of an aqueous solution of guest molecule into the solution of anionic polymer and multivalent cationic and allowing aging for a period ranging between 0-30 minutes at temperature ranging between 25-35° C. followed by adding aqueous solution of calcium salt and salt of carbonate with a concentration ranging between 0.01-0.1M, subsequently allowing aging the mixture as obtained for a period ranging between 30 minutes-15 hours at room temperature ranging between 25-35° C. to get precipitate of calcium carbonate; separating calcium carbonate as obtained by centrifugation at speed ranging between 8000-10000 rpm and washing with water followed by drying at room temperature ranging between 25-35° C. to obtain calcium carbonate microstructure.

In another embodiment of the present invention, wherein mol ratio of $Ca^{2+}:CO_3^{2-}$:poly(aspartate):penta(L-lysine):tetracycline used is 1:1:0.23:0.15:–0.11.

In another embodiment of the present invention, guest molecule used is selected from the group consisting of tetracycline, chlorhexidine hydrochloride and doxorubicin hydrochloride.

In another embodiment of the present invention, the calcium carbonate microstructure display fluorescence due to entrapped dye conjugated polymer or dye conjugated cationic oligomer or the encapsulated guest molecule as required for imaging applications.

In another embodiment of the present invention, calcium carbonate microstructures loaded with a guest molecule releases drug form the microstructure in controlled manner by the addition of a buffer solution comprised of phosphate buffer of pH 7.

BRIEF DESCRIPTION OF THE DRAWINGS

The present invention is illustrated in FIGS. 1 to 6 of the drawing(s) accompanying this specification. In the drawings like reference numbers/letters indicate corresponding parts in the various figures.

DETAILED DESCRIPTION OF THE INVENTION

Figure 1:
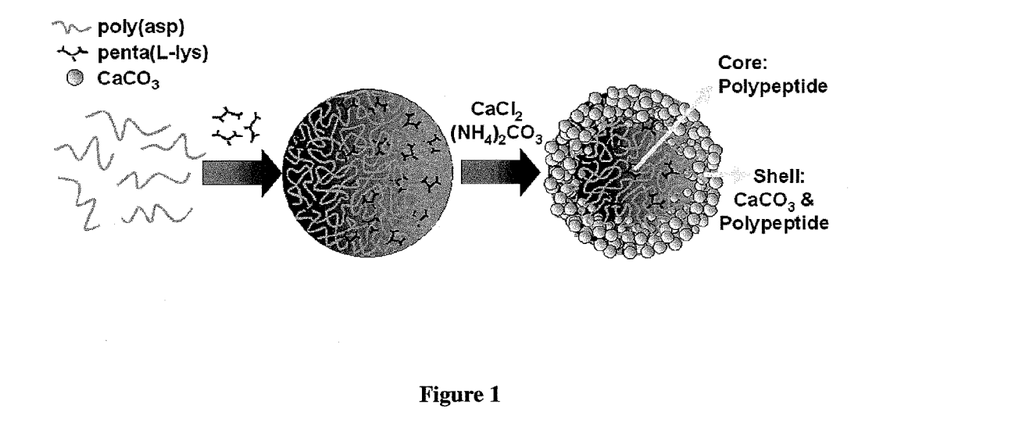
FIG. 1 represents Schematic illustration of the assembly process, in which anionic polymers ionically crosslink with cationic oligomer forming macromolecular assembly, which further template the $CaCO_3$ mineralization generating.

In the present invention calcium carbonate microstructures were synthesized under mild reaction conditions such as 25-35° C., atmospheric pressure, aqueous medium and pH 6-8, which is particularly suitable for use in biomedical applications such as drug encapsulation. The process involves a macromolecular assembly of polyanions with multivalent cationic species in an aqueous solution to which an aqueous solution containing salts of $Ca^{2+}$ is added followed by an aqueous solution containing salts of $CO_3^{2-}$ (FIG. 1). The anionic polymer comprised of but not limited to poly(aspartate) with a M. Wt. of 5-50 kD, concentration of 1-5 mg/ml. The multivalent cationic species comprised of but not limited to peptide oligomers of the type penta(L-lysine) or organic molecules of the type tetraethylenepentamine with a concentration of 1-5 mg/ml. The salts of $Ca^{2+}$ can be with anions such as chloride, sulfate, nitrate etc. with a concentration of 0.01-0.1 M and salts of $CO_3^{2-}$ can be with cations such as ammonium, sodium, potassium etc. with a concentration of 0.01-0.1 M. The synthesized calcium carbonate microstructures have morphology comprised of but not limited to spherical morphology with a core-shell structure where in the core is comprised of the anionic polymer and multivalent cationic oligomer, and the shell is comprised of the anionic polymer, multivalent cationic oligomer and $CaCO_3$.

To encapsulate a guest molecule comprised of but not limited to a drug such as tetracycline, an aqueous solution of which is added before addition of the salts of $Ca^{2+}$ and $CO_3^{2-}$ to form guest molecule loaded calcium carbonate microstructures. The synthesized calcium carbonate microstructures may display fluorescence either because of a dye conjugated polymer or cationic oligomer such as FITC tagged Poly(aspartate) or FITC tagged penta(L-lysine) which are used to form the macromolecular assembly, or the fluorescence can be due to the encapsulated guest molecule such as tetracycline. The fluorescent microstructures can be utilized in imaging applications. The release profile of the drug loaded calcium carbonate microstructures shows a controlled and sustained drug release depending upon the salts present in the buffer used for the study or the pH of the medium. The tetracycline loaded calcium carbonate microstructures exhibit antibacterial activity against various Gram-positive and Gram-negative bacterial strains.

Figure 2:
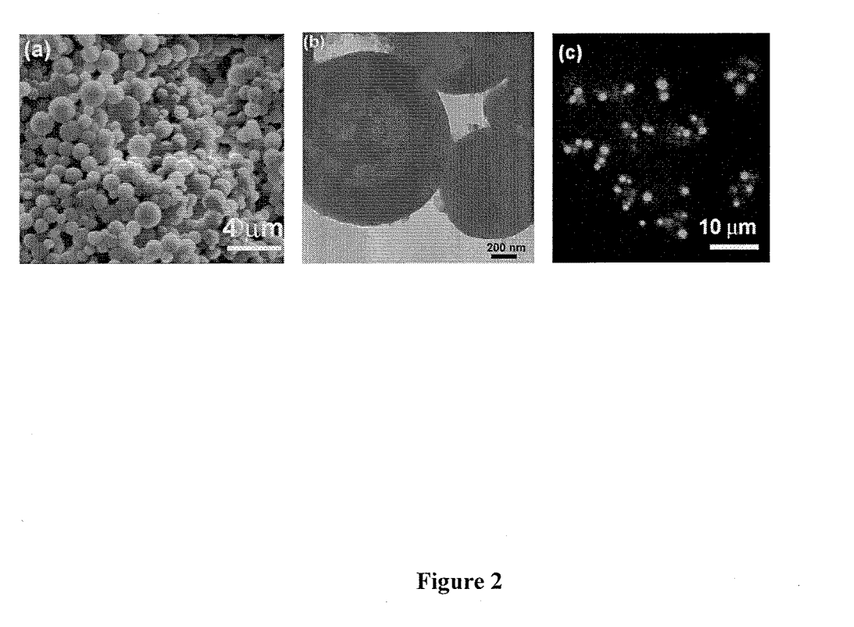
FIG. 2 represents (a) SEM, (b) HRTEM and (c) Confocal images of $CaCO_3$ microstructures prepared in the presence of poly(aspartate) and penta(L-lysine) with the samples aged for 15 hours.

The calcium carbonate microstructures formed by using poly(aspartate) and penta(L-lysine) from solutions containing $CaCl_2$ and $(NH_4)_2CO_3$ are shown in FIG. 2. The FT-IR spectrum of the sample displays characteristic band of the vaterite phase at 877 $cm^{-1}$ in addition to a broad band at 1070 $cm^{-1}$ ($v_1$, the symmetric stretch in noncentrosymmetric structure) indicating amorphous phase of $CaCO_3$. The band at 1426.5 can be assigned to an asymmetric stretching vibration of the carbonate groups and $Ca^{2+}$ ions. The Micro-Raman reveals a broad band at 1082 $cm^{-1}$ which is assigned to symmetric stretching vibration ($v_1$) mode of carbonate group. This is the strongest band for all the three polymorphs of calcium carbonate. The broadening of this band is attributed to presence of amorphous phase in contrast to the crystalline counterparts which exhibit very sharp peaks [(a) Addadi, L.; Raz, S.; Weiner, S. Adv. Mater. 2003, 15, No. 12, 959. (b) Huang, S.-C.; Naka, K.; Chujo, Y. Langmuir 2007, 23, 12086]. The crystalline phases were further characterized by XRD. The XRD pattern mainly exhibits characteristic reflections for vaterite and traces of calcite phase. The FT-IR further shows signature of amide linkages and methylene groups in polypeptides. Thus while mineralizing the $CaCO_3$ the polypeptide is entrapped in the structure. The total organic content in the mineralized sample is 15.22 Wt. % as estimated from thermo gravimetric analysis. The yield of $CaCO_3$ obtained with 30 min aging is 30.14 wt %, which with further aging up to 15 h increases to 43.21 Wt %.

The sample prepared with poly(aspartate) tagged with a dye (FITC) shows green fluorescence under a confocal microscope clearly indicating the presence of the polyanion inside the spheres. The polyanion and the cationic oligomer form the core while the mineralized $CaCO_3$ together with the polyanion and cationic oligomer make the shell wall of the core-shell structure. In contrast, when the sample was prepared in the absence of poly(aspartate) but in presence of penta(L-lysine)

distorted rhombohedra were formed, whereas in a control experiment without any additives perfect rhombohedra were formed.

The general importance of proteins and peptides in biomineralization has been demonstrated by many in-vitro studies. Their task is to control the nucleation, growth, polymorph and orientation of the inorganic compounds. For example, the extraction of soluble proteins from the aragonite layer of nacre and subsequent application as a $CaCO_3$ crystallization additive resulted in aragonite precipitation instead of the calcite, clearly demonstrating the importance of the organic matrix [(a) Falini, G.; Albeck, S.; Weiner, S.; Addadi, L. Science 1996, 271, 67-69. (b) Belcher, A. M.; Wu, X. H.; Christensen, R. J.; Hansma, P. K.; Stucky, G. D.; Morse, D. E. Nature 1996, 381, 56]. Similarly chiral crystals of calcite were formed taking pure D- or L-aspartic acid due to preferential binding of amino acid enantiomers to the particular surfaces which provide both geometrical and chemical symmetry [Orme, C. A.; Noy, A.; Wierzbicki, A.; McBride, M. T.; Grantham, M.; Teng, H. H.; Dove, P. M.; DeYoreo, J. J. Nature 2001, 411,775]. Gehrke et. al showed that synthetic polymer poly(asp) can take over some of the biopolymer functions known in natural systems like nacre [Gehrke, N.; Nassif, N.; Pinna, N.; Antonietti, M.; Gupta, H.; Colfen, H. Chem. Mater. 2005, 17, 6514]. The function of poly(aspartate) is intermediary stabilization of amorphous $CaCO_3$ (ACC) nanoparticles which are regarded as key intermediates in a variety of in vitro crystallization reactions. The preferential adsorption of the polypeptide was presumed to change the surface energies of different crystal faces, which subsequently results in modification of the crystallization process by simultaneously delaying crystal nucleation and growth to form metastable phases and also a variety of nonequilibrium morphologies [(a) L. Dai, X. Cheng, L. B. Gower Chem. Mater., 2008, 20, 6917; (b) L. Dai, X. Cheng, L. B. Gower Chem. Mater., 2008, 20 (22), 6917)].

As the concentration of poly(aspartate) was doubled a pure vaterite phase was obtained, thus supporting the above fact that polyanion is responsible for the stabilization of vaterite, a metastable phase. Further, when the reaction was carried out only in the presence of poly(aspartate) without penta(L-lysine) as counter-cation a mixed vaterite and calcite phase similar to that formed in the presence of both the additives was obtained. But, the morphology of the formed calcium carbonate consisted of spheres and particles of irregular morphologies. Interestingly, when the sample was subjected to sonication for TEM analysis the microspheres were found to be not stable and collapsed into discrete particles of size <50 nm. A similar observation by Zhang et. al., have earlier been reported and it is believed that Vander Waals force and hydrogen bonding are the main driving forces for the nanoparticle assembly and the soft nature of assembled nanoparticles allow the mobility and rearrangement of poly(aspartate) capped nanoparticles [Zhang, Z.; Gao, D.; Zhao, H.; Xie, C.; Guan, G.; Wang, D.; Yu, S.-H. J. Phys. Chem. B 2006, 110, 8613]. Quite contrastingly, in our case the $CaCO_3$ microspheres obtained in presence of both poly(aspartate) and penta(L-lysine) were stable under sonication. The counter-cation thus provides the stability by virtue of its ionic interaction with polyanion which holds the structure intact.

The formation of spherical particles in the former case can be explained by the fact that poly(aspartate) being negatively charged can bind with $Ca^{2+}$ to give spherical aggregates under experimental conditions and the addition of $CO_3^{2-}$ results in formation of spherical $CaCO_3$ microspheres. But in the later, a macromolecular assembly of poly(aspartate) with penta(L-lysine) generates prior to their interaction with $Ca^{2+}$ ions. This can be seen from the Dynamic light scattering (DLS) studies where the size distribution plot shows the formation of the aggregates having hydrodynamic-sizes in the range 500-4000 nm. After addition of $CaCl_2$ and $CO_3^{2-}$ salt, the generated $CaCO_3$ spheres had a similar size distribution as well. This experiment clearly illustrate the templating effect in which calcium carbonate particles nucleated and grew within the self-assembled polymer network. The fact that a core-shell structure is formed, suggests for a diffusion-limited penetration of the mineralizing ions into the polymer assembly to construct a shell wall, in which the mineralized nanoparticles are interspersed between several outer layers of polypeptide matrix (FIG. 1).

Figure 5:
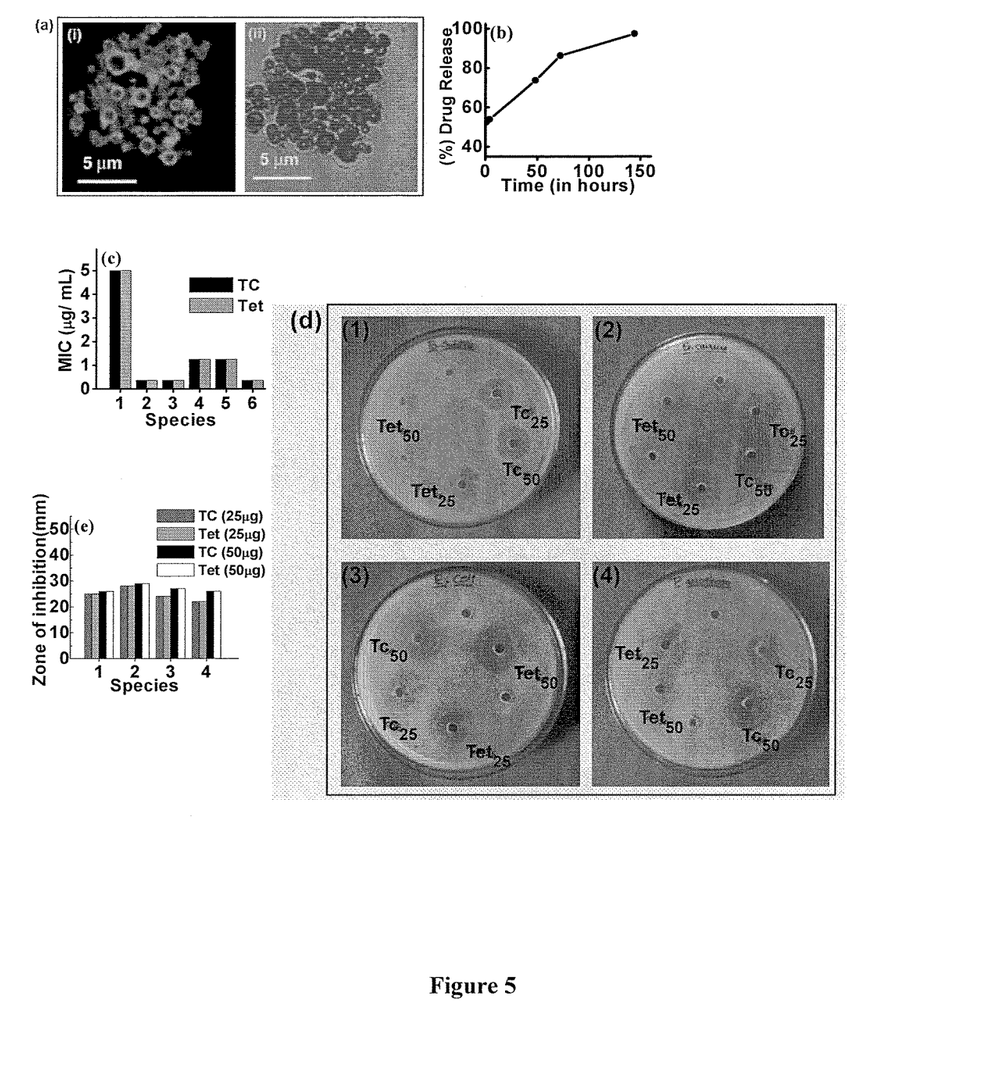
FIG. 5 represents (a) Tetracycline loaded CaCO3 microspheres; (i) confocal and (ii) bright field images. (b) Drug release profile of tetracycline loaded CaCO3 spheres in PBS buffer. (c) Minimum inhibitory concentrations (MIC) for various bacterial strains: (1) *B. subtilis*, (2) *S. aureus*, (3) *S. epidermidis*, (4) *E. coli*, (5) *P. aeroginosa* and (6) *K. pneumoniae*. (d) Visual images of zones of inhibition and (e) Comparison of the antibacterial activity from zone of inhibition. (1) *B. subtilis*, (2) *S. aureus*, (3) *E. coli*, and (4) *P. aeroginosa*. TC and Tet represents free and encapsulated tetracycline in CaCO3 microspheres, respectively and the subscripts as the amount of sample in µg.

These stable $CaCO_3$ microstructures were then utilized for encapsulation of a guest molecule such as tetracycline. The tetracycline was first added to the suspension containing poly (aspartate) and penta(L-lysine). The ionic interaction of tetracycline with the aggregates facilitates its penetration and further addition of $CaCl_2$ followed by $(NH_4)_2CO_3$ wraps them up to form the drug encapsulated $CaCO_3$ microspheres. A strong absorbance at 1605 $cm^{-1}$ in FT-IR indicates the C—C multiple bond stretching in aromatic ring of tetracycline. The fluorescence emanating from tetracycline clearly indicates its presence mainly located in the shell wall of the microspheres (FIG. 5a). From UV-VIS spectroscopy the tetracycline loading efficiency in the $CaCO_3$ microspheres was determined to be 62.27 Wt %.

The in vitro time dependent drug release studies were carried in PBS buffer (pH=7.4) at 37° C. From the drug release profile (FIG. 5b) it can be seen that the release of tetracycline from the $CaCO_3$ is time dependent. There is an initial burst release of 52.5% of the drug followed by slow release up to 144 hours. As tetracycline is used for treatment of bacterial infections associated with bones this type of profile is highly desirable where an immediate high dose is required followed by a slow release. The initial burst release of drug may be due to the presence of various anions such as phosphate in the PBS buffer. These ions can complex with $Ca^{2+}$ to leach them out thereby break the host matrix to induce an initial burst release of the drug. The deformation of these $CaCO_3$ microspheres was verified by scanning electron microscopy.

The tetracycline encapsulated $CaCO_3$ spheres were tested for their antimicrobial activity against both Gram-positive and Gram-negative microbial strains. The minimum inhibitory concentration (MIC) values for various strains are in the order S. aureus~S. epidermidis~E. coli<P. aeroginosa~K. pneumoniae<B. subtilis (FIG. 5(c)). From the disk diffusion assay the zone of inhibition (in mm) at the concentration of 25 µg/mL of the tetracycline loaded $CaCO_3$ for various strains was calculated (FIGS. 5(d & e)). Both MIC and zone of inhibition studies show that the antibacterial efficacy of the tetracycline loaded $CaCO_3$ spheres is similar to that of bare tetracycline.

Hence the calcium carbonate microstructures with activity for example, the encapsulated drug for therapeutic activity and the fluorescence for imaging can be useful in biomedical and other application.

The following examples are given by way of illustration of the working of the invention in actual practice and should not be construed to limit the scope of the present invention in any way.

Example-1

Synthesis of Calcium Carbonate Microstructures with a Spherical Morphology with a Core-Shell Structure In a typical synthesis to 200 µL poly(aspartate) (2 mg/mL), 200 µL, of penta(L-lysine) (2 mg/mL) was added. This mixture was then aged for 30 min at 27° C. To this mixture 200 μL of aqueous CaCl$_2$ (0.05 M) was added followed by addition of 200 μL of (NH$_4$)$_2$CO$_3$ (0.05 M). The molar ratio of the components added was 1 Ca$^{2+}$:1 CO$_3^{2-}$:0.3 poly(aspartate):0.2 penta(L-lysine). The pH of the mixture was 8.2. This mixture was then aged for 15 hours at 27° C. The calcium carbonate precipitate then obtained was centrifuged at a speed of 9000 rpm and washed 6 times with de-ionized water and dried at 27° C. The yield of CaCO$_3$ obtained with 30 min ageing was 30.14 wt %, which with further ageing up to 15 hours increased to 43.21 wt %. The synthesized calcium carbonate microstructures have spherical morphology with a core-shell structure where in the core is comprised of the anionic polymer and multivalent cationic oligomer, and the shell is comprised of the anionic polymer, multivalent cationic oligomer and CaCO$_3$ (FIGS. 2(a, b)).

Example-2

Synthesis of Calcium Carbonate Microstructures with a Spherical Morphology with a Core-Shell Structure In a typical synthesis to 200 μL poly(aspartate) (2 mg/mL), 200 μL of penta(L-lysine) (2 mg/mL) was added. This mixture was then aged for 0 min at 27° C. To this mixture 200 μL of aqueous CaCl$_2$ (0.05 M) was added followed by addition of 200 μL of (NH$_4$)$_2$CO$_3$ (0.05 M). The molar ratio of the components added was 1 Ca$^{2+}$:1 CO$_3^{2-}$:0.3 poly(aspartate):0.2 penta(L-lysine). The pH of the mixture was 8.2. This mixture was then aged for 15 hours at 27° C. The calcium carbonate precipitate then obtained was centrifuged at a speed of 9000 rpm and washed 6 times with de-ionized water and dried at 27° C. The synthesized calcium carbonate microstructures have spherical morphology with a core-shell structure where in the core is comprised of the anionic polymer and multivalent cationic oligomer, and the shell is comprised of the anionic polymer, multivalent cationic oligomer and CaCO$_3$.

Example-3

Synthesis of Fluorescent Calcium Carbonate Microstructures with a Spherical Morphology with a Core-Shell Structure In a typical synthesis to 200 μL FITC-tagged poly(aspartate) (2 mg/mL) 200 μL of penta(L-lysine) (2 mg/mL), was added. This mixture was then aged for 30 min at 27° C. To this mixture 200 μL of CaCl$_2$ (0.05 M) was added followed by addition of 200 μL of (NH$_4$)$_2$CO$_3$ (0.05 M). The molar ratio of the components added were 1 Ca$^{2+}$:1 CO$_3^{2-}$:0.3 FITC-poly(aspartate):0.2 penta(L-lysine). This mixture was then aged for a time interval of 15 hours at room temperature. The calcium carbonate precipitate then obtained was centrifuged at a speed of 9000 rpm and washed 6 times with de-ionized water and dried at 27° C. The synthesized fluorescent calcium carbonate microstructures have spherical morphology with a core-shell structure where in the core is comprised of the anionic polymer and multivalent cationic oligomer, and the shell is comprised of the anionic polymer, multivalent cationic oligomer and CaCO$_3$ (FIG. 2c).

Example-4

Figure 3:
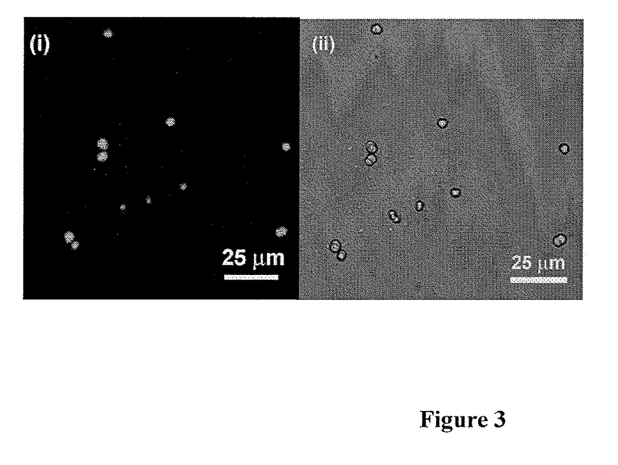
FIG. 3 represents (i) Confocal and (ii) Bright-field images of $CaCO_3$ microstructures prepared in the presence of poly (aspartate) and FITC-tagged penta(L-lysine) with the samples aged for 15 hours.

Synthesis of Fluorescent Calcium Carbonate Microstructures with a Spherical Morphology In a typical synthesis to 200 μL poly(aspartate) (2 mg/mL), 200 μL of FITC-tagged penta(L-lysine) (2 mg/mL), was added. This mixture was then aged for 30 min at 27° C. To this mixture 200 μL of CaCl$_2$ (0.05 M) was added followed by addition of 200 μL of (NH$_4$)$_2$CO$_3$ (0.05 M). The molar ratio of the components added were 1 Ca$^{2+}$:1 CO$_3^{2-}$:0.3 poly(aspartate):0.2 FITC-penta(L-lysine). This mixture was then aged for a time interval of 15 hours at room temperature. The calcium carbonate precipitate then obtained was centrifuged at a speed of 9000 rpm and washed 6 times with de-ionized water and dried at 27° C. The synthesized fluorescent calcium carbonate microstructures have spherical morphology with a core-shell structure where in the core is comprised of the anionic polymer and multivalent cationic oligomer, and the shell is comprised of the anionic polymer, multivalent cationic oligomer and CaCO$_3$ (FIG. 3).

Example-5

Mechanical Stability of Spherical CaCO$_3$ Microstructures

The mechanical stability of the CaCO$_3$ microstructures was tested by ultrasonicate an aqueous suspension of the sample prepared in Example 1. For comparison, CaCO$_3$ microspheres were also prepared following the Example 1 but in absence of penta(L-lysine).

Figure 4:
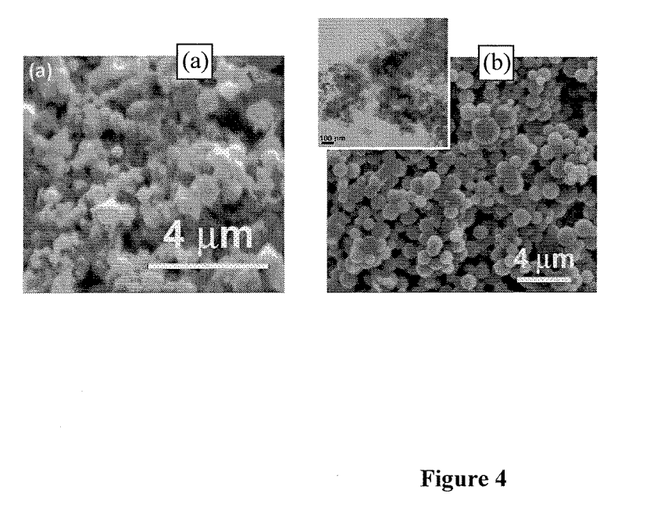
FIG. 4 represents (a) SEM (inset TEM) and (b) SEM images of the ultrasonicated $CaCO_3$ microstructures prepared in the absence and presence of penta(L-lysine), respectively using poly(aspartate) as the mineralizer. Ultrasonication of the samples was done for 15 min.

For ultrasonication 100 mg of the above two samples were taken in separate beakers and 10 mL of de-ionized water was added to each and the mixture was sonicated for 30 min in a bath sonicator. The samples obtained after sonication were analysed by SEM and TEM. As shown in FIG. 4, the CaCO$_3$ microspheres synthesized in Example-1 were found to be stable under ultrasound, whereas the spherical CaCO$_3$ microspheres prepared in absence of penta(L-lysine) broke into discrete particles under ultrasound irradiation.

Example-6

Synthesis of Calcium Carbonate Microstructures Loaded with Tetracycline Drug

In a typical synthesis to 200 μL of poly(aspartate) (2 mg/mL), 200 μL of penta(L-lysine) (2 mg/mL), added. To this mixture 250 μL of 5.63 mM tetracycline solution (dissolved in 0.01M HCl) was added. Then 250 μL of CaCl$_2$ (0.05 M) followed by 250 μL of (NH$_4$)$_2$CO$_3$ (0.05 M) were added to the above mixture. The molar ratio of the components added were 0.23 poly(aspartate):0.15 penta(L-lysine):0.11 Tetracycline:1 Ca$^{2+}$:1 CO$_3^{2-}$. This mixture was then aged for 30 min at 27° C. The precipitate then obtained was centrifuged at a speed of 9000 rpm and washed 6 times with de-ionized water and dried at 27° C. The synthesized tetracycline loaded calcium carbonate microstructures have spherical morphology with a core-shell structure as described in example 1 where in the tetracycline drug is mostly confined to the shell (FIG. 5a).

Example-7

Drug Release and Antibacterial Activity of Tetracycline Loaded Calcium Carbonate Microstructures For the tetracycline release from CaCO$_3$ microstructures, the dissolution test was performed in PBS buffer (pH 7.4), with a stirring speed of 100 rpm at 37±0.2°. After each interval of time a predetermined amount of supernatant was taken out which was then replaced by freshly prepared PBS buffer. The percentage release of drug was calculated by finding out the concentration of drug in the released medium at particular time intervals by UV-Vis spectroscopic analysis From the drug release profile (FIG. 5b) it can be seen that the release of tetracycline from the $CaCO_3$ microstructures is time dependent. There is an initial burst release of 52.5% of the drug within 1.0 hour followed by a slow release with 97.4% of the drug released at 144 hour.

Antimicrobial activity of tetracycline loaded $CaCO_3$ microstructures and bare tetracycline was tested against the Gram-negative bacterial strains of E. coli (MTCC 443), K. pneumoniae (MTCC 618) and P. aeroginosa (MTCC 1688) and also with number of Gram-positive bacterial strains of B. subtilis (MTCC 441), S. aureus (MTCC 96), and S. epidermidis (MTCC 435). Culture of test organisms were maintained on Nutrient agar slants and were sub-cultured in Petri dishes prior to testing. The Minimum Inhibitory concentration (MIC) was determined by broth dilution method (NC-CLS Methods, 2009) [Linday M E, practical introduction to microbiology, London: E & F. N Spon Ltd; 1962, p 177]. Antibacterial activity of the synthesized tetracycline containing $CaCO_3$ and bare tetracycline were determined by the well diffusion method [NCCLS Methods for Dilution Antimicrobial susceptibility tests for bacteria, that grows aerobically, eighth ed. NCCLS, Villanova, Pa., 2009, Approved standard M 07-A8.]. Inhibition zones were measured and the diameter was calculated in millimeter. Three replicates were maintained for each treatment. The minimum inhibitory concentration (MIC) values for various strains are in the order S. aureus~S. epidermidis~E. coli<P. aeroginosa~K. pneumoniae<B. subtilis (FIG. 5c). From the disk diffusion assay the zone of inhibition (in mm) at the concentration of 25 µg/mL of the tetracycline loaded $CaCO_3$ for various strains was calculated (FIGS. 5d & e). Both MIC and zone of inhibition studies show that the antibacterial efficacy of the tetracycline loaded $CaCO_3$ spheres is similar to that of bare tetracycline.

Example-8

Synthesis of Calcium Carbonate Microstructures with a Doughnut Like Morphology

Figure 6:
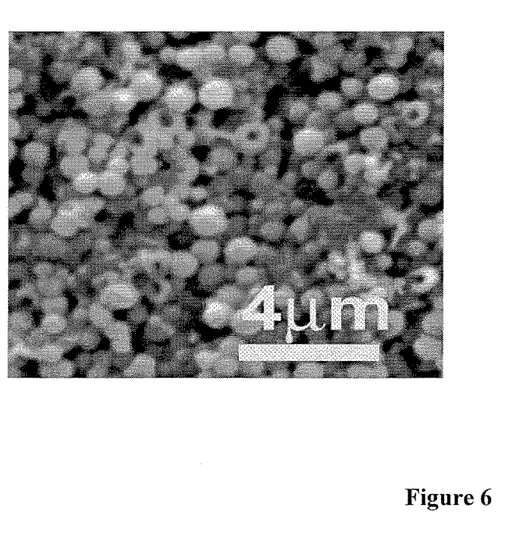
FIG. 6 represents SEM image of doughnuts shaped $CaCO_3$ microstructures prepared in the presence of poly(aspartate) and tetraethylenepentamine (tetrene) with the samples aged for 15 hours.

In a typical synthesis to 200 µL of poly(aspartate) (2 mg/mL), 200 µL of tetraethylenepentamine (tetrene) (2 mg/mL) was added. To this mixture 200 µL of $CaCl_2$ (0.05 M) was added followed by addition of 200 µL of $(NH_4)_2CO_3$ (0.05 M). The molar ratio of the components added were 1 $Ca^{2+}$:1 $CO_3^{2-}$:0.3 poly(aspartate):0.96 tetrene. This mixture was then aged for a time interval of 15 hours at 27° C. The calcium carbonate precipitate then obtained was centrifuged at a speed of 9000 rpm and washed 6 times with de-ionized water and dried at 27° C. The synthesized calcium carbonate microstructures have doughnut morphology as shown in FIG. 6.

The main advantages of the present invention are:
A process to synthesize calcium carbonate microstructures with a core-shell morphology utilizing a macromolecular assembly of anionic polypeptide with cationic peptide oligomer to concurrently template and hold to stabilize the mineralized structure in an aqueous solution containing salts of $Ca^{2+}$ and $CO_3^{2-}$.
The formation takes place under the green conditions of aqueous medium, near neutral pH, ambient temperature and pressure suitable for encapsulation of sensitive molecules like drugs, proteins, enzymes, dyes etc.
It is a "green process" to have the encapsulation of the tetracycline drug in distilled water.
Such an easily adaptable method overcomes limitations of traditional encapsulation strategies, as it requires no post-treatments and multi step processes but allows for in-situ encapsulation of the guest molecule such as tetracycline at ambient conditions without affecting the mineralization process.
The calcium carbonate microstructures are stable as does not get collapsed under ultrasound irradiation, as has been the case for the microstructure obtained without the cationic peptide oligomer.
The calcium carbonate microstructure displays fluorescence either because of the entrapped dye conjugated polymer or the drug such as tetracycline as required for imaging applications
The tetracycline loaded calcium carbonate microstructure shows in vitro time dependent drug release profile in which there is an initial burst release of the drug followed by slow release. For treatment of bacterial infections associated with bones this type of profile is highly desirable where an immediate high dose is required followed by a slow release.
The tetracycline loaded sample exhibits excellent antibacterial activity against both Gram-positive and Gram-negative microbial strains and hence can be utilized for therapeutic applications.

The main use of the methodology and the materials are in encapsulation applications such as encapsulating and controlled release of pharmaceuticals for sustained and controlled delivery for therapeutic applications, encapsulation of fluorescent molecules for biomedical imaging applications. Also can find application in cosmetics and various health and beauty products, and in preparation of household products such as soaps, detergents and brighteners.

We claim:

1. A stable, controlled release calcium carbonate core-shell microstructure consisting of:
   a shell consisting of
      an anionic polymer selected from the group consisting of poly(aspartate) and fluorescein isothiocyanate (FITC)-tagged poly(aspartate) with molecular weight of 5-50 kD,
      a multivalent cationic oligomer selected from the group consisting of tetraethylenepentamine, penta(L-lysine) and fluorescein isothiocyanate (FITC)-tagged penta(L-lysine) and $CaCO_3$;
         wherein said anionic polymer and said cationic oligomer are ionically cross-linked to form a macromolecular assembly and said $CaCO_3$ penetrates said assembly to form said shell; and
   a core consisting of
      said anionic polymer and
      said multivalent cationic oligomer;
         wherein said anionic polymer and said cationic oligomer are ionically cross-linked to form a macromolecular assembly.

2. The calcium carbonate microstructure as claimed in claim 1, wherein the multivalent cationic oligomer is in the range of 5-7%, said anionic polymer is in the range of 9-12% and said $CaCO_3$ is in the range of 76-81% by weight.

3. The calcium carbonate microstructure as claimed in claim 1, wherein morphology of the microstructure is spherical or doughnut.

4. The calcium carbonate microstructure as claimed in claim 3, wherein the diameter of the spheres ranges between 0.5-4.0 micrometers.

5. The calcium carbonate microstructure as claimed in claim 1, wherein the microstructure is mechanically stable under ultrasonication as compared to structures obtained in absence of the cationic oligomer.

6. The microstructure of claim 1, wherein said shell further comprises an encapsulated guest molecule, wherein said quest molecule is a drug selected from the group consisting of tetracycline, chlorohexidine hydrochloride and doxorubicin hydrochloride.

7. The microstructure of claim 6, wherein said drug is tetracycline.

* * * * *